US 7,837,654 B2

(12) United States Patent
Shumate et al.

(10) Patent No.: US 7,837,654 B2
(45) Date of Patent: Nov. 23, 2010

(54) PRECISION SENSING AND TREATMENT DELIVERY DEVICE FOR PROMOTING HEALING IN LIVING TISSUE

(75) Inventors: Daniel L. Shumate, Huntsville, AL (US); Paul B. Ruffin, Toney, AL (US); John Curtis Fulda, Huntsville, AL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1168 days.

(21) Appl. No.: 11/311,585

(22) Filed: Dec. 15, 2005

(65) Prior Publication Data

US 2007/0142714 A1    Jun. 21, 2007

(51) Int. Cl.
*A61M 5/00* (2006.01)
(52) U.S. Cl. .................................................. 604/173
(58) Field of Classification Search ............... 604/173, 604/182; 600/182
See application file for complete search history.

(56) References Cited

U.S. PATENT DOCUMENTS

| | | | |
|---|---|---|---|
| 4,191,184 A | | 3/1980 | Carlisle |
| 4,461,281 A | | 7/1984 | Carson |
| 4,798,738 A | * | 1/1989 | Yafuso et al. ............... 427/2.11 |
| 5,312,328 A | * | 5/1994 | Nita et al. .................... 604/22 |
| 6,419,654 B1 | * | 7/2002 | Kadan ......................... 604/27 |
| 2005/0261568 A1 | * | 11/2005 | Hular et al. ................. 600/407 |

OTHER PUBLICATIONS

Deshmukh et al., Continuous micromixer with pulsatile micropumps, Jun. 4-8, 2000,Solid-State Sensor and Actuator Workshop, p. 73-76.*
Ajay A Deshmukh, Dorian Liepmann, Albert P Pisano, Continuous Micromixer With Pulsatile Micropumps, Solid-State Sensor and Actuator Workshop, Jun. 4-8, 2000, Hilton Head, SC.

* cited by examiner

*Primary Examiner*—Nicholas D Lucchesi
*Assistant Examiner*—Pritesh Patel
(74) *Attorney, Agent, or Firm*—Jack K. Greer, Jr.; Michael K. Gray

(57) ABSTRACT

A microneedle insertable in a target cell tissue, including a manipulative end maintained exterior of cell tissue and an insertion end positionable in or adjacent of target cell tissue. A plurality of microtubes are bundled to pass through the needle body and extend to respective distal ends grouped proximally interior of the insertion end. A sensing fiber is extendable from means for sensing for passage through the needle body to a distal end capable of sensing cell tissue parameters. The insertion end and the bundled microtube and sensing fiber distal ends are positionable in or adjacent of cell tissue thereby providing rapid evaluation of cell parameters by optic fiber sensing, fiber sampling of cell parameters, and precise delivery of therapeutic fluids or additional treatment measures. A method is also disclosed of precisely positioning a microneedle having a plurality of microtubes and sensing fibers therein for evaluating and treating cell tissue.

16 Claims, 7 Drawing Sheets

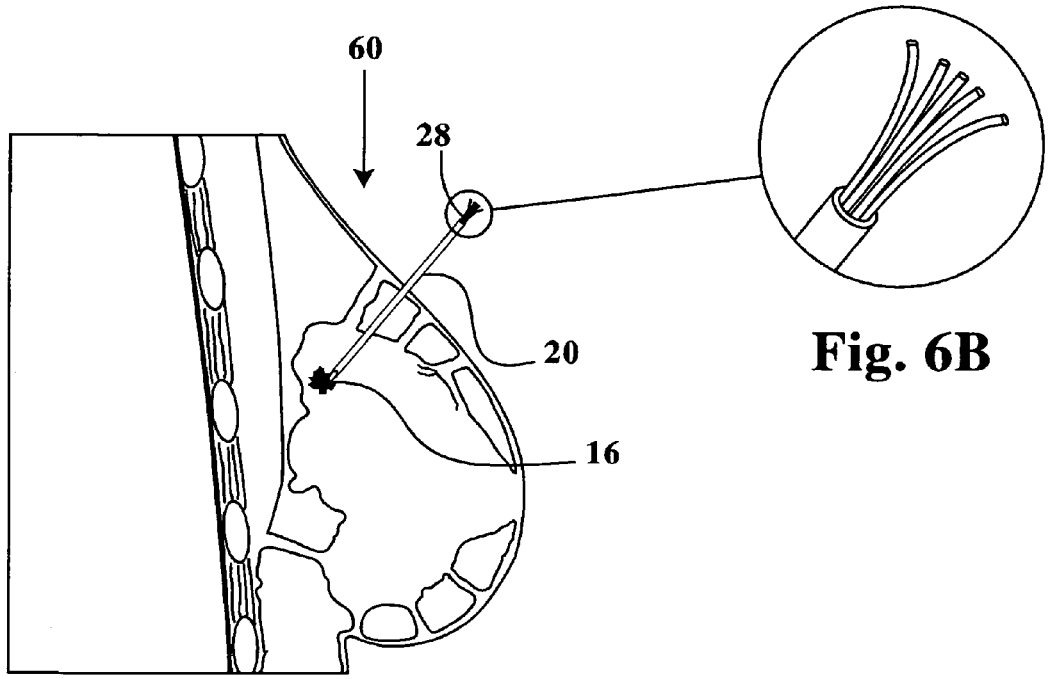
Fig. 6B
Fig. 6A
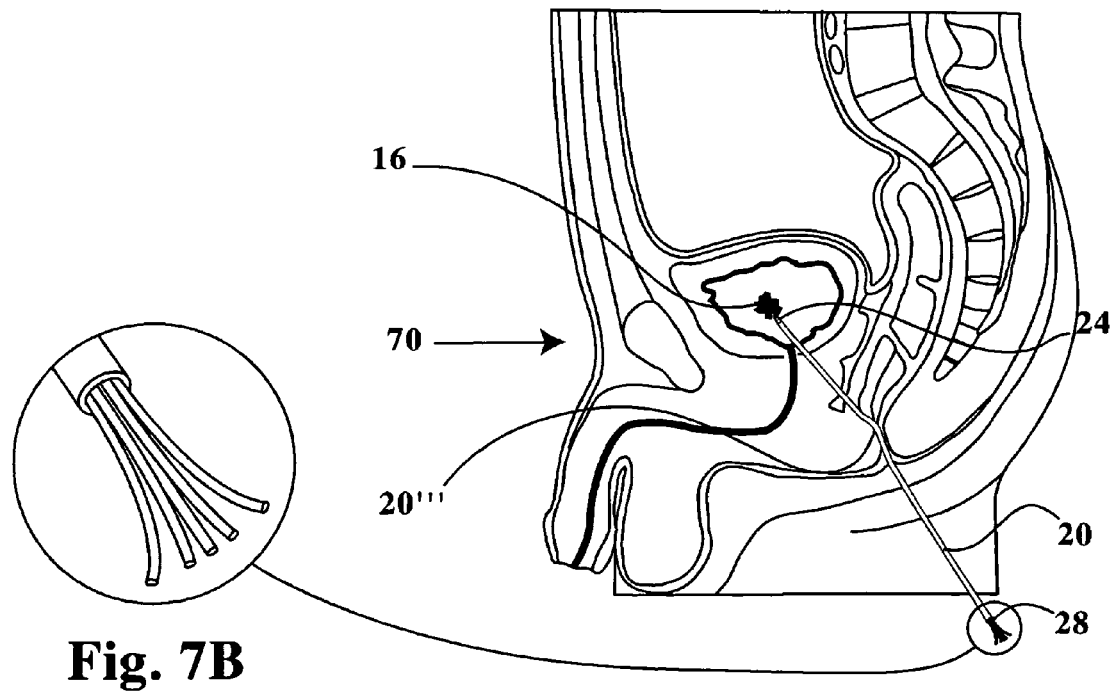
Fig. 7B
Fig. 7A

PRECISION SENSING AND TREATMENT DELIVERY DEVICE FOR PROMOTING HEALING IN LIVING TISSUE

STATEMENT REGARDING FEDERALLY SPONSORED RESEARCH OR DEVELOPMENT

The invention described herein may be manufactured, used and licensed by or for the Government for governmental purposes without the payment to the inventors and/or the assignee of any royalties thereon.

CROSS-REFERENCE TO RELATED APPLICATIONS

Not Applicable.

BACKGROUND OF THE INVENTION

1. Field of the Invention

The present invention relates to a micro-sized needle which is insertable through a patient's dermal layer for sampling of tissue in vivo. More specifically, the present invention relates to a needle having a micrometer internal diameter through which a plurality of sensing probes and delivery tubules are extended for monitoring cell parameters at the needle distal end and for delivering therapeutic fluids directly into tissue cells.

2. Description of the Related Art

Prior medical procedures for delivery of therapeutic fluids to treat systemic diseases include utilizing a hypodermic needle for delivery of mixtures of medication by means of an intravenous (IV) drip into a patient's vein. If the disease is diagnosed early and is localized in one organ or a group of cells within a patient, then systemic distribution of the medication within the patient by the arteries and veins is not efficient when compared to delivery of medication by hypodermic needle inserted proximal of the diseased cells. Typical hypodermic needles utilized in prior medical procedures include needles having an outer diameter (OD) of approximately 300 micrometers, and having an internal diameter (ID) of approximately 150 micrometers. One type of a medication infusion system is illustrated in U.S. Pat. No. 4,191,184 (the '184 patent), issued to J. A. Carlisle. The infusion regulation system of the '184 patent provides for regulating, monitoring, and control of IV infusion of fluids in a patient. The infusion regulation system provides a volume control apparatus including a peristaltic pump unit providing fluid flow through divaricated tubing for delivery of measured volumes of fluids to an outlet tube attached to a cannula inserted in a patient's vein. The system of the '184 patent provides for systemic infusion of a relatively large volume of pre-mixed fluid and lacks the ability to deliver one or more therapeutic fluids in precise volumes to a tumor or numerous groups of diseased cells.

Prior medical procedures for positioning of probes by means of an incision into a patient includes insertion of optic fibers in a patient to view a tumor, or insertion of surgical instruments to excise a tumor. One example includes a surgical instrument inserted through a sleeve member positioned in an incision proximal of a joint member as illustrated in U.S. Pat. No. 4,461,281 (the '281 patent), issued to R. W. Carson. The arthroscopic surgical apparatus of the '281 patent includes a hollow cannula having an ID of about 5 mm for insertion therein of a blade shaped tip of an elongated shaft. The cannula provides a tubular guide to position the blade shaped tip in a knee joint and to facilitate penetration by the blade shaped tip through the subcutaneous tissue and fascia of the knee joint during joint tissue repair. Additional cutting tools or optic fibers are utilized by inserting through a second cannula positioned proximal of the knee joint and adjacent to first cannula, or the blade shaped tip of the elongated shaft is removed from first cannula followed by insertion of a second cutting tool or an optic fiber for viewing the joint tissue repair. The apparatus of the '281 patent does not provide for one needle which remains positioned in an incision during a surgical procedure, with one needle having multiple channels therein for positioning of optic fibers for viewing while concurrently positioning one or more treatment instruments against the joint tissue undergoing repair.

Recent medical procedures utilizing probes inserted into a patient's organs includes positioning of laser probes for eye surgery as illustrated in U.S. Pat. No. 5,643,250 (the '250 patent), issued to F. E. O'Donnell, Jr., and in U.S. Pat. No. 6,520,955 (the '955 patent), issued to M. Reynard. The '250 patent illustrates a laser probe which includes a fiber optic channel and an infusion port for irrigating solutions to be infused into an eye during laser surgery on cornea tissue. The laser probe is manipulated as a hand piece for insertion of the probe tip through the cornea of a patient's eye, in order to position the probe tip having a fiber optic opening therein in close proximity to the target cataract tissue. The laser probe diameter may not allow insertion through numerous layers and densities of tissues disposed between a dermal surface and internal organs disposed medially within a patient. The '955 patent illustrates a process and apparatus for removing cataract tissue in an eye and for injecting a lens replacement material into the eye lens to fill the intralenticular space. The apparatus of the '955 patent includes a needle having dual cannula oriented as coaxial annular conduits through which chemicals and enzymes are delivered into cataract tissue. A separate focused laser is utilized to destroy the cataract tissue, followed by destroyed cataract tissue being removed by aspiration through an aspiration instrument or through a coaxial annular conduit of the needle. The diameter and configuration of the dual cannula needle may limit precise insertion into a specific tumor in an organ after needle insertion through multiple layers and tissue densities within the patient.

A need exists for a minimally intrusive microneedle which is positionable into a cell or a group of cells, and is capable of actively retrieving samples for monitoring of current cell conditions while remaining inserted in the cell or group of cells. There is a further need for a microneedle having a plurality of microtubules providing channels for optic fibers, channels for samples intracellular conditions, and channels for delivery of therapeutic fluids into the cell in order to promote healing of, or selective suppression of specific cells.

BRIEF SUMMARY OF THE INVENTION

A microneedle is disclosed for insertion in a patient without significantly disrupting overlying tissue layers in order to precisely position an insertion end adjacent to a target cell mass or to position the insertion end in a target cell tissue. The microneedle includes a manipulative end maintained exterior of the target cell tissue, with the manipulative end in fluid communication with means for fluid flow and at least one fluid flow source, and/or in optical or electrical communication with a cell parameter monitoring source and one or more therapeutic treatment sources. The microneedle insertion end includes a tapered length having a diminishing outer diameter to allow positioning in or adjacent to the target cell tissue. A needle body joins the manipulative and insertion ends.

The microneedle includes one or a plurality of microtubes disposed in a bundled configuration within the needle body. The microtubes have distal ends grouped proximal to and interior of the microneedle insertion end. The plurality of microtubes include at least one fluid flow microtube extending to a distal end disposed proximal of the microneedle insertion end, thereby allowing repetitive delivery of a primary treatment fluid into, or removal of cell fluids from the target cell tissue. A second fluid flow microtube is readily incorporated within the plurality of microtubes, with the second fluid flow microtube extending to a second flow end disposed at the microneedle insertion end, thereby allowing repetitive delivery of secondary treatment fluid into or removal of cell fluids treated with the primary treatment fluid delivered by the first fluid flow microtube. Each fluid flow microtube is coupled with the means for fluid flow source such as a microfluidic pump capable of fluid delivery rates of about five microliters/minute.

The microneedle further includes one or more sensing fibers extended within the microneedle body, with one sensing fiber having an optic fiber end disposed at the microneedle insertion end, and an optical detector and transmission fiber extending from the microneedle insertion end and extending to the microneedle manipulative end. Additional sensing fibers extending through the microneedle body can include a pH sensing fiber having a pH assay end at the microneedle insertion end, a thermal fiber having a heat transfer end at the microneedle insertion end positionable within or adjacent to the target cell tissue. Another embodiment of the microneedle includes an oxygen sensor fiber extended through the microneedle body, with an oxygen sensor end at the microneedle insertion end, and/or a temperature sensing fiber extended through the microneedle body, with a temperature sensor end at the microneedle insertion end. Further embodiments of the microneedle include a vibration fiber extended to a vibratory end at the microneedle insertion end.

Implementation of the microneedle includes the insertion end being positioned within or adjacent to the target cell tissue, thereby positioning the plurality of microtubes distal ends and associated sensing fibers and fluid flow microtubes within the target cell tissue or adjacent to the target tissue mass. The sensing fibers provide evaluation of the cell tissue internal conditions while the fluid flow microtubes provide flow paths for delivery of one or more treatment fluids to the target cell tissue, thereby adjusting the cell tissue internal conditions to preferred levels of pH, oxygen content, temperature, and osmotic balance to facilitate healing of diseased and/or damaged cell tissue. Upon the advice by medical personnel after monitoring of the cell tissue internal conditions with the microneedle, an exact dose of therapeutic medicine, oxygen, vibration, and/or thermal transfer is dispensed through the microneedle, with resulting promotion of cellular healing or poisoning of malignant cells. The microneedle is readily removed and discarded, or reused after sterilization.

BRIEF DESCRIPTION OF THE DRAWINGS

The present invention is illustrated in the drawings in which like element numbers represent like parts in each figure, including:

FIG. 6A is a cross-sectional view of a human female breast in which the microneedle insertion end is positioned in target cell tissue into which a plurality of microtubes and/or microfibers distal ends extend;

FIG. 6B is an exploded view of a manipulative end of the microneedle of FIG. 6A, from which a plurality of microtubes and/or microfibers proximal ends extend;

FIG. 7A is a cross-sectional view of a human male reproductive system in which the microneedle insertion end is positioned in target cell tissue into which a plurality of microtubes and/or microfibers distal ends extend;

FIG. 7B is an exploded view of a manipulative end of the microneedle of FIG. 7A, from which a plurality of microtubes and/or microfibers proximal ends extend;

DETAILED DESCRIPTION OF THE INVENTION

Figure 1:
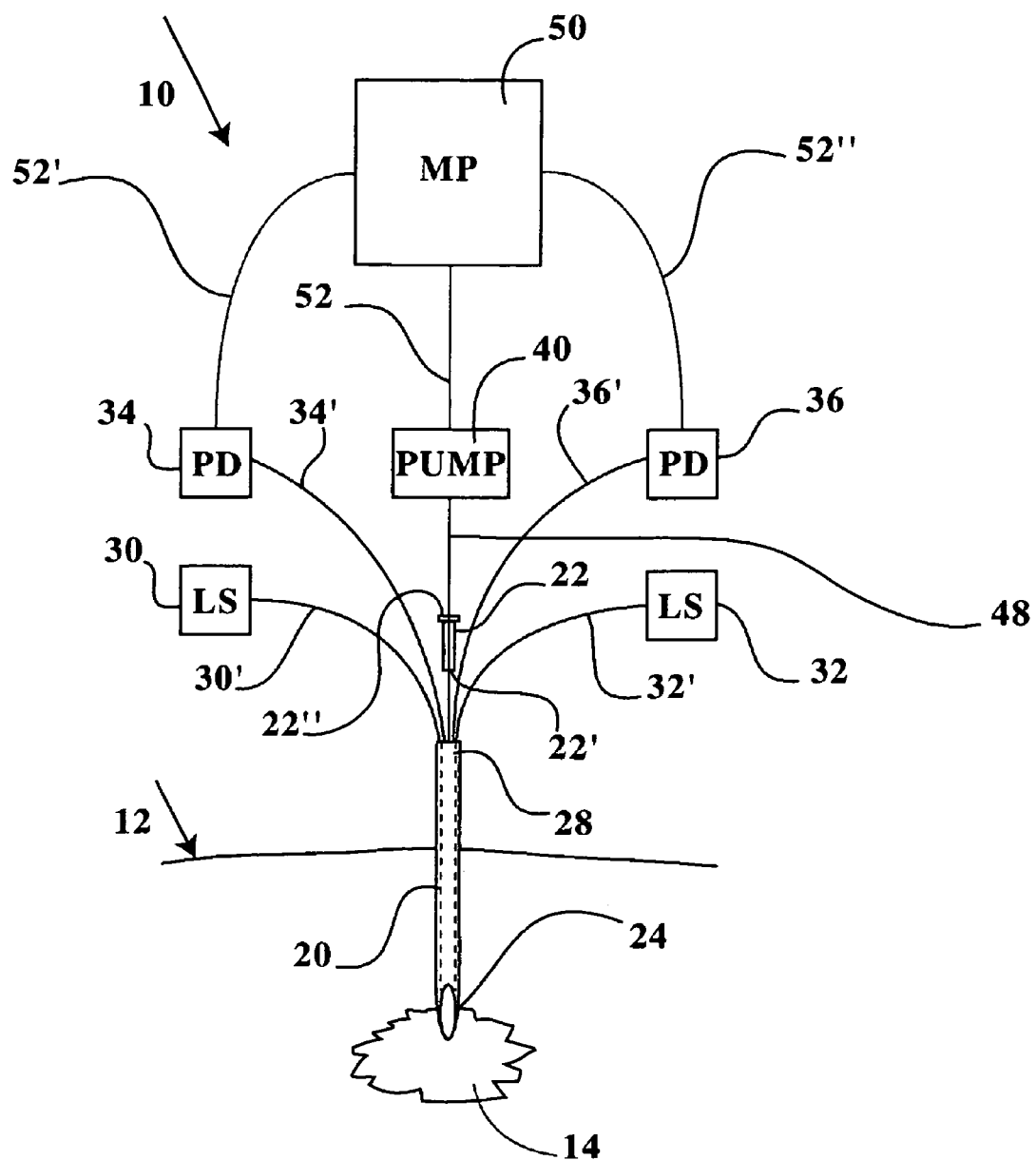
FIG. 1 is a side view of one embodiment of the present invention, illustrating a microneedle having a manipulative end connected with means for fluid flow, a cell parameter monitoring source, and one or more therapeutic treatment sources.

Referring now to FIGS. 1-8B, a multiple channel needle and delivery system 10 is disclosed, including a microneedle 20 sized for insertion into cell tissue within a patient without significantly disrupting a patient's dermal surface 12 or underlying tissue layers proximal of a target cell tissue 14 or a target tumor mass 16. The microneedle 20 includes a distal insertion end 24 having an elongated and tapered end opening 26 (see FIGS. 2, 3A and 3B), thereby readily allowing positioning of the insertion end 24 and end opening 26 within the target cell tissue 14, a tumor mass 16, or an internal organ or joint (see FIGS. 6-8B). The microneedle 20 includes a proximal end, identified herein as a manipulative end 28, which is maintained exterior of the target cell tissue 14 during positioning of the insertion end 24. The manipulative end 28 is sized in internal diameter (ID) to receive therein one or more microtubes 48, 48', and/or one or more microfibers 30', 32', 34', 36'. The manipulative end 28 can be coupled with a stopper or spacer 22 inserted therein and having an insertion end 22' and a proximal end 22", serving as a block from exiting of tissue fluids from the manipulative end 28, and serving to maintain grouping of the plurality of microtubes and microfibers within the microneedle 20 during insertion through the patient's tissue layers and during positioning at the target cell tissue 14.

The microtube 48, 48' proximal ends are extended outwards from the manipulative end 28 for a sufficient distance to connect with means for fluid flow including a micropump 40 and at least one fluid flow source, thereby maintaining fluid communication between the micropump 40 and fluid flow source and at least one fluid flow microtube 48, 48' extended through a needle body interior 28'. The needle body includes a cross-section having a cylindrical, oval or multi-sided cross-section, extends a sufficient length to join the manipulative end 28 and insertion end 24. The main portion of the needle body 20 includes an OD 20" of up to about 150 micrometers (hereinafter, microns), and an ID 28" of up to about 120 microns. Additional embodiments for the main portion of the needle body 20 provide an alternative OD 20" of between about 80 microns to about 120 microns, and an alternative ID 28" of between about 70 microns to about 110 microns. The distal insertion end 24 forms an elongated and tapered end opening 26 with a cross-sectional dimension diminishing from about 110 microns to a distal end a cross-sectional dimension of about 70 microns. The needle body 20 is manufactured of a biocompatible material known to those skilled in the art, such as heat-treatable stainless steel, carbon steel, or carbon based materials.

The microneedle manipulative end 28 includes a sufficient ID 28" to retain therein one or more microtubes 48, 48', and/or one or more microfibers 30', 32', 34', 36' grouped in a space efficient bundled configuration within the needle body 20. Each microfiber includes an outer diameter of between about 40 microns to about 50 microns. Each microfiber includes a proximal end extended from the manipulative end 28 for connection with one or more means for sensing, such as one or more sensing devices including, but not limited to, a light source 30 and photodetector 34, and/or monitoring devices for assessing pH, oxygen content, temperature, and osmotic balance within the target cell tissue 14. Each respective microfiber is composed of a biocompatible material chosen by those skilled in the art to facilitate the function of each microfiber (i.e. optical transmission, detecting of pH, oxygen, etc.). The bundled configuration includes any combination of a microtube and a microfiber, or multiple microtubes and multiple microfibers in bundled combinations of three, five, seven, and up to nineteen combined microtubes and microfibers extended through the needle body interior 28' length. Each microtube and microfiber includes distal ends extended proximally of the interior surface 28''' of the insertion end 24 (see FIG. 2). One configuration for the distal ends is illustrated in FIGS. 3A and 3B, whereas one or more of microtubes and/or microfibers have distal ends extended outwards from the elongated and tapered end opening 26 of the insertion end 24 in order to facilitate interaction between the distal ends and the target cell tissue 14. In one embodiment, the multiple microtubes extended through the microneedle 20 include at least one fluid flow microtube 48 in fluid connection with the means for fluid flow, such as a micropump and fluid flow source. A second fluid flow microtube 48' is readily incorporated in the plurality of microtubes, with the second fluid flow microtube 48' extending to a second distal flow end disposed at the insertion end 24, thereby allowing constant or intermittent delivery of secondary treatment fluid into or removal of cell fluids from the target cell tissue 14 in coordination with the primary treatment fluid delivered by fluid flow microtube 48. The microtubes include an inside diameter of between about 50 microns to about 90 microns, with a smaller ID preferred when five or more microtubes are bundled within the needle body 20. The microtubes 48, 48' are manufactured of a biocompatible material known to those skilled in the art, such as heat-treatable stainless steel, carbon steel, or carbon based materials.

Figure 5:
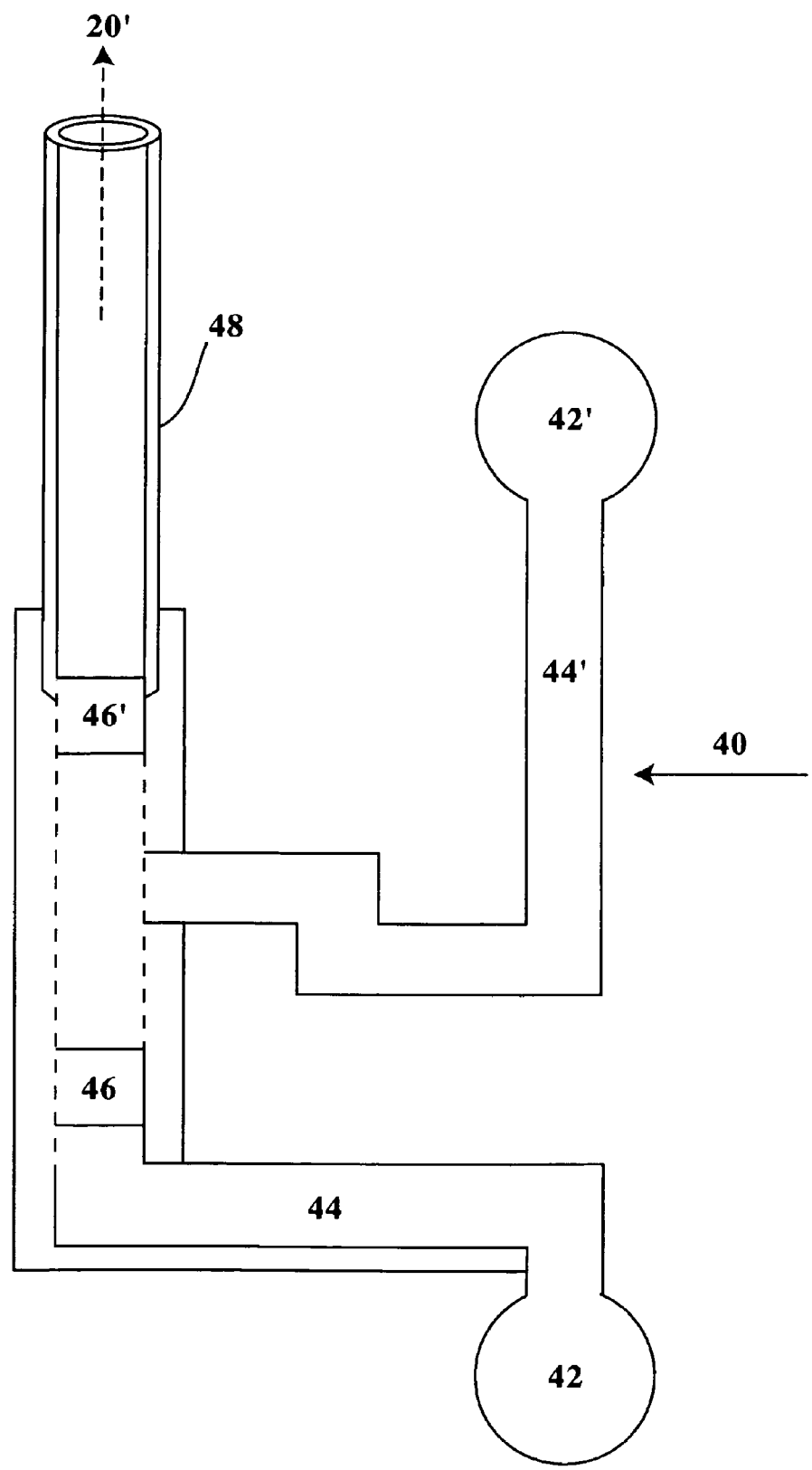
FIG. 5 is a schematic diagram of means for fluid flow including flow pump and fluid source in communication with at least one microtube as illustrated in FIG. 2.

The fluid flow source can include a pulsatile micropump 40 and micromixer known to those skilled in the art (see FIG. 5). The pump rate of the micropump 40 is readily adjustable by an operator of the microneedle 20 and by means of input to a microprocessor (MP) 50 (see FIG. 1), having a communication path 52 with micropump 40, and having communication paths 52', 52" with photodetectors 34, 36 of the delivery system 10, to provide a typical flow rate in a range of between about 1.5 microliters/minute to about five microliters/minute of a primary treatment fluid and/or second treatment fluid through the distal end of the fluid flow microtube 48 for delivery to the target cell tissue 14 or target tumor mass 16. As illustrated in FIG. 5, a pulsatile micropump 40 includes two inlet chambers 42, 42', each of about 800 microns in diameter, in which a bubble is created by polysilicon resistors on quartz which act as heaters in each chamber 42, 42'. Each bubble created serves as a micropiston to drive fluid from each chamber 42, 42' and into and through respective microchannels 44, 44'. The fluid flows through check valves 46, 46' which direct fluid flow movement from the inlet chambers 42, 42' to the output portion of the micropump 40, thereby directing fluid flow 20' into and through one or more microtubes 48, 48' extended through the microneedle 20 to the insertion end 24.

Figure 2:
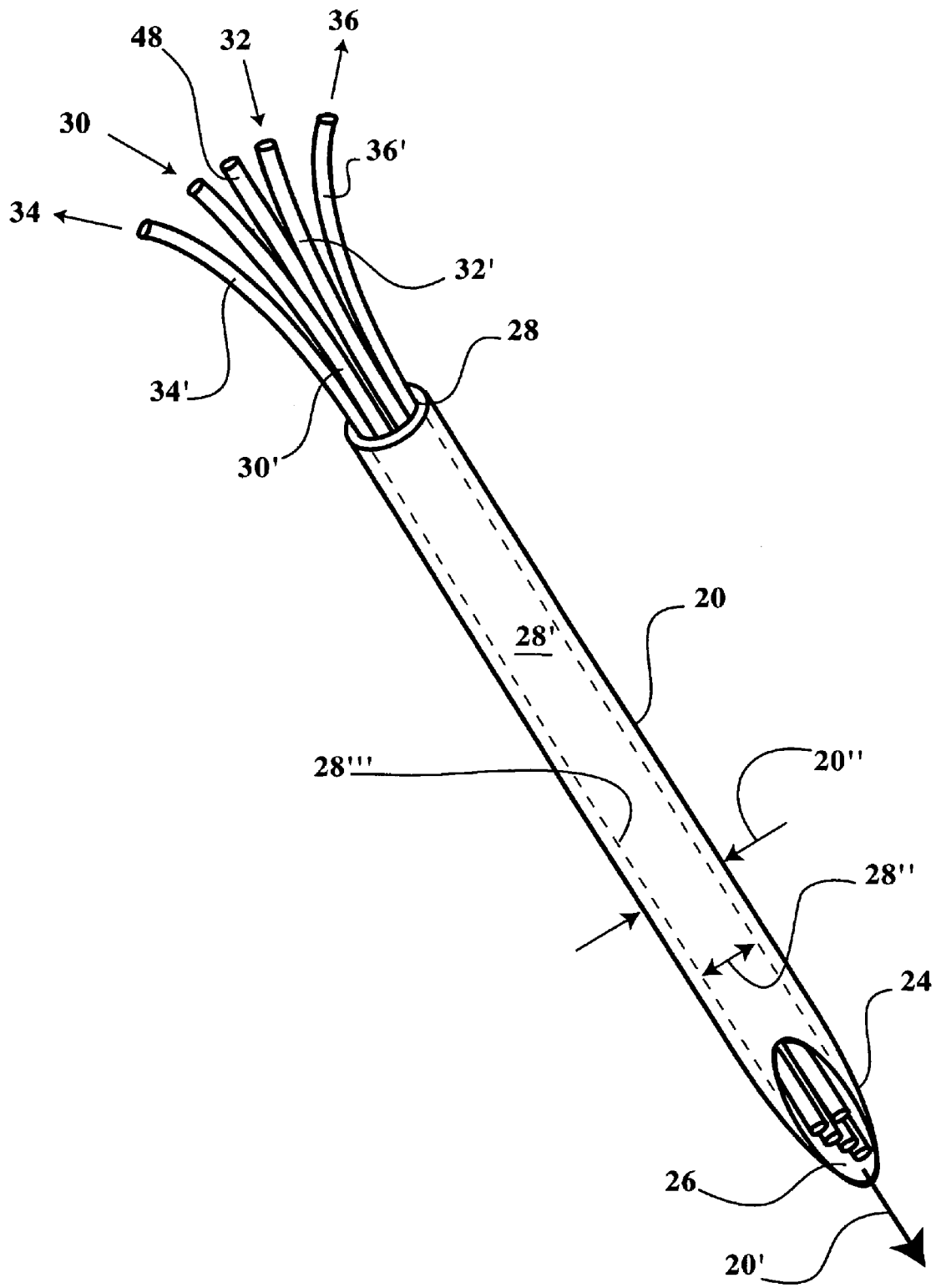
FIG. 2 is a perspective view of the microneedle of FIG. 1, illustrating a needle body in which a plurality of microtubes extend to a microneedle insertion end.
Figure 3A:
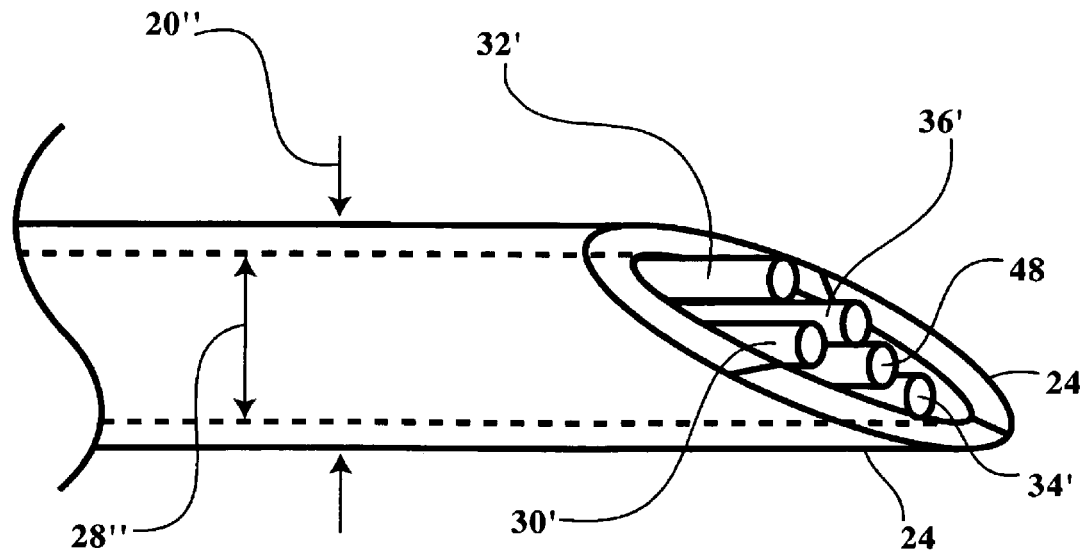
FIG. 3A is a side perspective view of the microneedle insertion end having a plurality of microtube distal ends disposed therein.
Figure 3B:
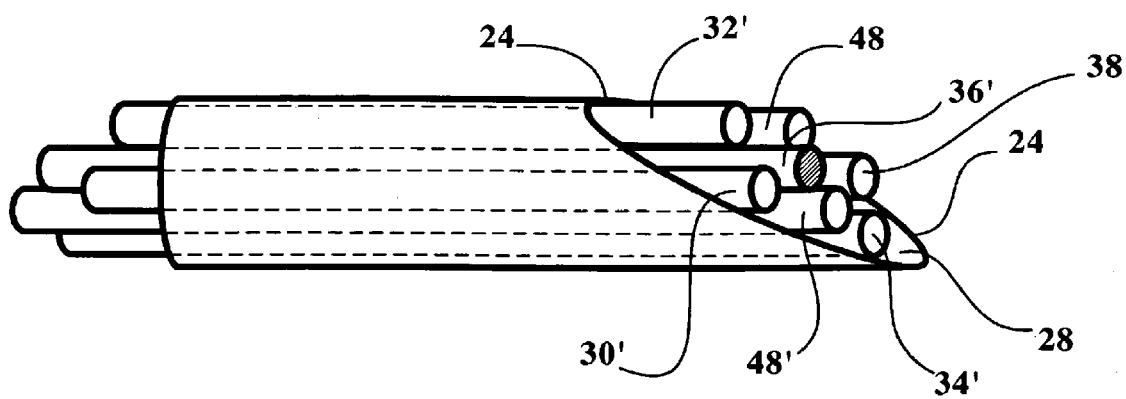
FIG. 3B is a side view of FIG. 3A, illustrating and internal diameter of the insertion end from which a staggered grouping of microtube distal ends extend.
Figure 4:
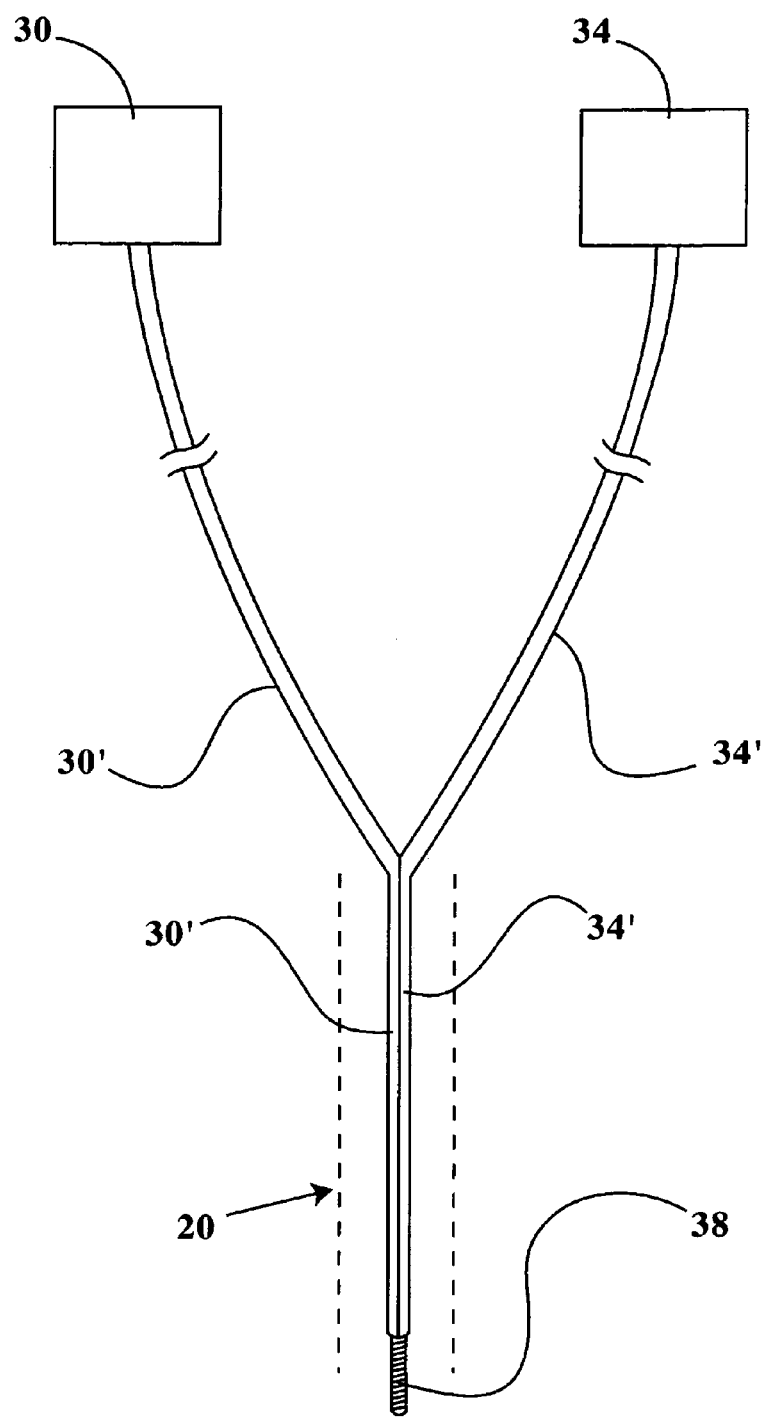
FIG. 4 is a side view of an optical fiber and detector in communication with one of the plurality of microtubes illustrated in FIG. 2.

The embodiments illustrated in FIGS. 2-3B include at least a first optical fiber 30' connected with a light source 30 positioned external of the patient. The first optical fiber 30' extends the interior length of the microneedle 20 to an optic fiber end disposed at the insertion end 24. Paired with the first optical fiber 30' is an optical detector fiber 34' extending from the optic fiber end, through the microneedle 20, and connected with a photodetector 34 (see FIGS. 1 and 4). In order to increase the optical viewing ability of the microneedle 20, a second optical fiber 32' can be included and connected with a second light source 32 positioned external of the patient. The second optical fiber 32' also extends the interior length of the microneedle 20 to a second optic fiber end (see FIGS. 3A and 3B), which is disposed at the insertion end 24. Paired with the second optical fiber 32' is a second optical detector fiber 36' extending from the optic fiber end 38, through the microneedle 20, and connected with a second photodetector 36 (see FIG. 1).

The plurality of microtubes and/or microfibers bundled within the microneedle 20 further includes an option for a pH sensing fiber to be retractably extended through the needle body interior 28' in order to position a pH assay distal end 38 at the insertion end 24 (see FIG. 3B). The pH sensing fiber can be configured as an optical fiber having a pH sensitive film or dye disposed on the distal end 38 (see FIG. 4), or configured as an electrical conductive fiber having a distal end sensitive to ionic concentration changes indicative of the pH within a target cell 14 or tumor mass 16. The optical fiber and pH sensing fiber configuration allows for optical signals to be continually or intermittently transmitted through the optical fiber until changes in the optical properties of the pH sensitive film or dye on the distal end is detected by detector 34, thereby indicating a pH change in the target cell 14 or tumor mass 16.

Additional embodiments for the plurality of microtubes and/or microfibers include a thermal fiber extended through the needle body interior 28', and having a heat transfer end positioned distally from the insertion end 24 to provide heat exchange within or adjacent to the target cell 14 or tumor mass 16. Also, an oxygen sensor fiber 58 can be extended through the needle body interior 28', with an oxygen sensor end extended from the insertion end 24. In addition, a vibratory fiber 54 can be through the needle body interior 28', with a vibratory distal end positioned distally from the insertion end 24 (see FIG. 3B). The vibratory distal end can be activated to provide internal vibration within the target cell 14 or tumor mass 16, to provide therapy or to selectively destroy the target tissue(s) without chemotherapy.

A method of precisely positioning a microneedle having a plurality of microtubes and sensing fibers therein for evaluating and treating target cell tissue is also disclosed. Implementation of the microneedle includes the insertion end being positioned within or adjacent to the target cell tissue, thereby positioning the plurality of microtubes distal ends and associated sensing fibers and fluid flow microtubes within the target cell tissue or adjacent to the target tissue mass. The sensing fibers provide evaluation of the cell tissue parameters by medical personnel, including optically viewing the cell tissue, and/or sensing the pH, oxygen content, temperature, or other significant cell parameters. The fluid flow microtubes provide flow paths for delivery of one or more treatment fluids to the target cell tissue, thereby adjusting the cell tissue internal conditions to preferred levels of pH, oxygen content, temperature, and/or osmotic balance to facilitate healing of diseased and/or damaged cell tissue. Upon the advice by medical personnel after monitoring of the cell tissue parameters with the microneedle, an exact dose of therapeutic medicine, oxygen, vibration, and/or thermal transfer is readily delivered through one or more of the microtubes of the microneedle, with resulting promotion of cellular healing or poisoning of malignant cells. The microneedle is readily removed and discarded, or reused after sterilization.

Figures 8A, 8B:
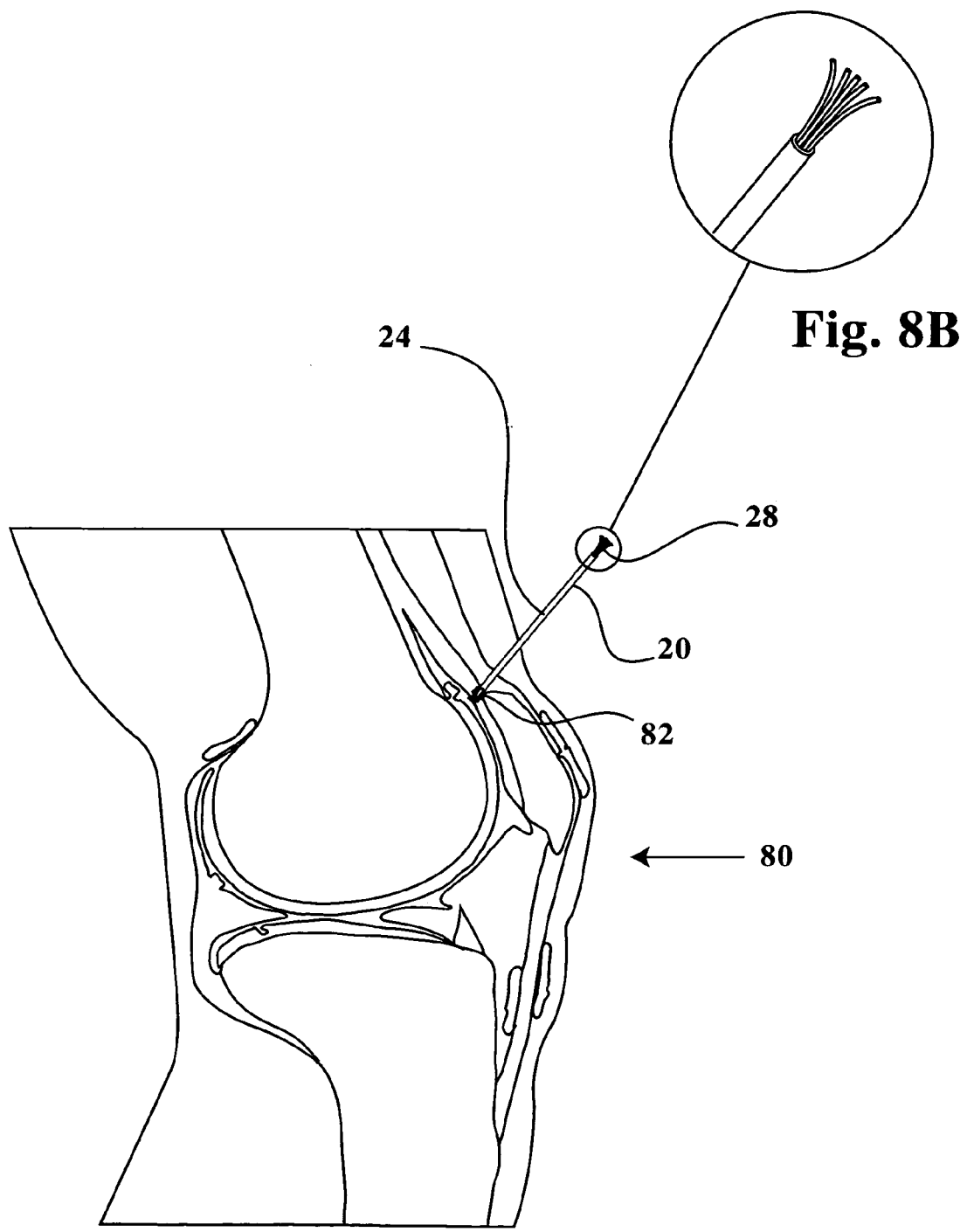
FIG. 8A is a cross-sectional view of a human knee joint in which the microneedle insertion end is positioned adjacent to torn tissue into which a plurality of microtubes and/or microfibers distal ends extend.
FIG. 8B is an exploded view of a manipulative end of the microneedle of FIG. 8A, from which a plurality of microtubes and/or microfibers proximal ends extend.

A multitude of applications are readily apparent to one skilled in the medical arts, including positioning of the microneedle in target cell tissue residing in any living organ which is not moving or has been stopped or slowed in movement. An example of one of many applications is illustrated in FIGS. 6A and 6B for inserting a microneedle 20 in order to assess and treat targeted cell tissue 14 in a human female breast 60. Another example of an application is illustrated in FIGS. 7A and 7B for inserting a microneedle 20 in order to assess and treat targeted cell tissue 14 in a human male reproductive system 70. The needle 20 in FIGS. 7A and 7B illustrates a needle body including a buckle or bend 20''' engineered and manufactured therein, to facilitate manipulation of the needle body and microtubes therein through a natural orifice and interior channels of a patient during needle into a patient. An additional application is illustrated in FIGS. 8A and 8B for inserting a microneedle 20 adjacent to a site of torn tissue 82 in a human knee joint 80, in order to assess, repair and/or remove the tissue 82. Further applications for the microneedle 20 include insertion in a shoulder, hip joint, or back vertebrae for repair of torn tissue or for treatment of calcified tissue. The described applications for a multiple channel needle and delivery system 10 are not intended to be all-inclusive, nor limiting to additional applications in humans and applications in mammals.

While numerous embodiments and methods of use for this invention are illustrated and disclosed herein, it will be recognized that various modifications and embodiments of the invention may be employed without departing from the spirit and scope of the invention as set forth in the appended claims. Further, the disclosed invention is intended to cover all modifications and alternate methods falling within the spirit and scope of the invention as set forth in the appended claims.

What is claimed is:

1. A needle insertable in a target cell tissue within a human or animal, comprising:
   a microneedle having a manipulative end maintained exterior of target cell tissue and having a fluid flow conduit extended through an interior of said microneedle, said fluid flow conduit in communication with means for fluid flow positioned exterior of the human or animal, said microneedle having an insertion end sized for positioning in or adjacent of target cell tissue and having a needle body having an outside diameter in a micron size range, said needle body joining said manipulative and insertion ends; and
   said fluid flow conduit including a plurality of microtubes extended in a compact bundled configuration through said needle body, said plurality of microtubes having respective distal ends grouped proximally interior of said insertion end and having respective microtube proximal ends extended from said manipulative end, including a first microtube proximal end and a second microtube proximal end separately in communication with means for fluid flow, thereby said first microtube providing a conduit for a microliter volume of a first fluid flow separate from and within said interior of said microneedle, said first fluid flow further separate from said second microtube providing a second conduit for a second microliter volume of a second fluid flow between a distal end of respective first and second microtube proximal ends extended from said manipulative end in communication with means for fluid flow;
   whereby said insertion end is positionable in or adjacent of target cell tissue with said plurality of microtubes distal ends positioned in or adjacent of target cell tissue, thereby providing cell tissue sampling for evaluation of target cell tissue parameters by separate fluid flow transfer of first and second fluid flow between said microneedle insertion end and said manipulative end, and further providing repetitive and coordinated delivery of first and second treatment fluid fluids into or adjacent of target cell tissue by transfer of treatment fluid fluids from means for fluid flow and through said first and second microtube of said plurality of microtubes without removal or reposition of said first and second microtube within said needle body.

2. The needle of claim 1 wherein said means for fluid flow including a pulsatile micropump and a micromixer in fluid flow communication with said proximal end of said at least one microtube, said micropump providing an adjustable pump rate for production of a fluid flow in a range of between about 1.5 microliters/minute to about five microliters/minute for passage through said distal end of at least one microtube of said plurality of microtubes.

3. The needle of claim 1, further comprising:
   said microneedle needle body including a cylindrical cross-section having an outside diameter of between about 70 microns to about 150 microns; and
   said microneedle insertion end including an elongated and tapered end opening sized in a range of a cross-sectional dimension of between about 70 microns to about 110 microns.

4. The needle of claim 1, further comprising:
   a sensing microfiber extended in said microneedle, and having a distal end disposed proximally interior of said insertion end for sensing cell parameters of the target cell tissue, said sensing microfiber having a proximal end extended from said manipulative end for connection with said means for sensing, and further including:
   an optic fiber extended within said needle body, said optic fiber having an optic fiber distal end disposed at said insertion end and having an optic signal transmission end in communication with a light source positioned exterior of the human or animal; and
   an optical detector fiber extended within said needle body, said optical detector fiber having an optic detector distal end and having an optic image transmission end in communication with a photodetector positioned exterior of the human or animal.

5. The needle of claim 4 wherein said sensing microfiber including a pH sensing fiber extended within said needle body, said pH sensing fiber having a pH assay distal end disposed at said insertion end, and having a proximal pH fiber end in communication with said means for sensing, whereby said pH assay distal end being capable of sensing pH in the target cell tissue.

6. The needle of claim 4 wherein said sensing microfiber including a thermal fiber extended through said needle body, said thermal fiber having a heat transfer distal end disposed at said insertion end, and having a proximal thermal fiber end in communication with said means for sensing, whereby said heat transfer distal end being capable of heat exchange with the target cell tissue.

7. The needle of claim 4 wherein said sensing microfiber including an oxygen sensor fiber extended through said needle body, said oxygen sensor fiber having an oxygen sensing distal end disposed at said insertion end, and having a proximal oxygen sensor end in communication with said means for sensing, whereby said oxygen sensing distal end being capable of monitoring oxygen concentration in the target cell tissue.

8. The needle of claim 4 wherein said sensing microfiber including a vibratory fiber extended through said needle body, said sensing fiber having a vibratory distal end disposed distally from said insertion end, and having a proximal vibratory fiber end in communication with said means for sensing, whereby said vibratory distal end being capable of vibrating within the target cell tissue thereby providing therapy or selectively destroying the target cell tissue.

9. A microneedle insertable within or proximal to a target cell tissue, comprising:
a microneedle having a manipulative end maintained exterior of the target cell tissue and in fluidic communication with means for fluid flow, and having an insertion end sized for positioning in or adjacent of target cell tissue, and having a needle body joining said proximal and insertion ends; and
a plurality of microtubes extended in a compact bundled configuration through said needle body, said microtubes having respective distal ends grouped proximally interior of said insertion end, said plurality of microtubes including a first and second fluid flow microtube providing separated delivery of primary and secondary treatment fluids to the target cell tissue, said second fluid flow microtube allows separate delivery of secondary treatment fluid into or separate removal of cell fluids from target cell tissue in coordination with delivery of primary treatment fluid through said first fluid flow microtube; and
at least one sensing fiber in said needle body and having a distal end disposed proximally interior of said insertion end disposed proximally interior of said insertion end for repetitive sensing of cell parameters of the target cell tissue;
whereby said insertion end is positionable in or adjacent of target cell tissue with said microtubes distal ends and said at least one sensing fiber distal end being positioned in or adjacent of target cell tissue, thereby providing rapid evaluation of the cell tissue parameters by said at least one sensing fiber and further providing repetitive and coordinated delivery of primary and secondary treatment fluids within or adjacent of target cell tissue and providing removal of target cell fluids by transfer through said first and/or second fluid flow microtubes without removal or reposition of said first and second fluid flow microtubes within said microneedle insertion end positionable in or adjacent of target cell tissue.

10. The microneedle of claim 9 wherein said means for fluid flow including a pulsatile micropump having a micromixer therein, said micropump providing an adjustable pump rate for production of a fluid flow rate in a range of between about 1.5 microliters/minute to about five microliters/minute for passage through at least one distal end of said plurality of microtubes.

11. The microneedle of claim 9 further comprising:
said microneedle needle body including a cylindrical cross-section having an outside diameter of between about 70 microns to about 150 microns; and
said microneedle insertion end including an elongated and tapered end opening sized in a range of a cross-sectional dimension of between about 70 microns to about 110 microns.

12. The microneedle of claim 9 wherein said at least one sensing fiber includes:
an optic fiber extended within said needle body, said optic fiber having an optic fiber distal end disposed at said insertion end, and having an optic signal transmission end in communication with a light source positioned exterior of the human or animal; and
an optical detector fiber extended within said needle body, said optical detector fiber having an optic detector distal end, and having an optic image transmission end in communication with a photodetector positioned exterior of the human or animal.

13. The microneedle of claim 9 wherein said at least one sensing fiber further includes:
a pH sensing fiber extended within said needle body, said pH sensing fiber having a pH assay distal end disposed at said insertion end, and having a proximal pH fiber end in communication with said means for sensing;
a thermal fiber extended through said needle body, said thermal fiber having a heat transfer distal end disposed at said insertion end, and having a proximal thermal fiber end in communication with said means for sensing;
an oxygen sensor fiber extended through said needle body, said oxygen sensor fiber having an oxygen sensing distal end disposed at said insertion end, and having a proximal oxygen sensor end in communication with said means for sensing; and
a vibratory fiber extended through said needle body, said sensing fiber having a vibratory distal end disposed distally from said insertion end, and having a proximal vibratory fiber end in communication with said means for sensing.

14. A method of positioning a microneedle for evaluating and treating target cell tissue, comprising the steps of:
(a) providing a microneedle including an insertion end, a manipulative end and a needle body having an outside diameter in a micron size range, through which a plurality of microtubes and sensing fibers extend in a minimum sized bundled configuration, said microtubes and sensing fibers having distal ends grouped proximally interior of said insertion end, said plurality of microtubes including a first microtube and a second microtube, each first and second microtube providing a separate path for a first therapeutic fluid and a second therapeutic fluid bounded respectfully by said first and second microtubes positioned within said needle body;
(b) positioning said insertion end within or adjacent of the target cell tissue, thereby positioning the plurality of microtube distal ends and bundled sensing fibers distal ends within or adjacent of the target cell tissue;

(c) evaluating the target cell tissue parameters with said sensing fibers, said step of evaluating including selecting one or more steps including optically viewing the target cell tissue, sensing pH in the target cell tissue, measuring oxygen content in the target cell tissue, and monitoring osmotic balance in the target cell tissue;

(d) delivering fluid flow including first and second therapeutic fluids to target cell tissue by separately transferring said first and second therapeutic fluids through said first and second microtubes, whereby said step of delivering providing an exact dose of said first and second therapeutic fluids to a preferred portion of the target cell tissue without removal or repositioning said microneedle within or adjacent of the target cell tissue; and (e) adjusting the target cell tissue internal conditions upon delivering of said first and second therapeutic fluids, thereby adjusting the target cell tissue to preferred levels of pH, oxygen content, temperature, and/or osmotic balance to facilitate healing of cell tissue.

15. The method of claim 14 further comprising the step of treating the target cell tissue by vibrating a vibratory fiber extended through said needle body, said vibratory fiber having a vibratory distal end disposed distally from said insertion end, and having a proximal vibratory fiber end in communication with said means for sensing, whereby said step of vibrating being capable of vibrating said vibratory distal end within the target cell tissue thereby providing therapy or selectively destroying the target cell tissue.

16. The method of claim 14, wherein said step of delivering including providing a pulsatile micropump and micromixer capable of providing an adjustable fluid flow rate in a range between about 1.5 microliters/minute to about five microliters/minute.

* * * * *